United States Patent
Mackenzie

(10) Patent No.: US 9,066,820 B2
(45) Date of Patent: Jun. 30, 2015

(54) FLEXION ENHANCEMENT MEMBER FOR PROSTHETIC OR ORTHOTIC LINER OR SLEEVE AND ASSOCIATED METHODS

(75) Inventor: Craig M. Mackenzie, Orlando, FL (US)

(73) Assignee: EVOLUTION INDUSTRIES, INC., Orlando, FL (US)

( * ) Notice: Subject to any disclaimer, the term of this patent is extended or adjusted under 35 U.S.C. 154(b) by 657 days.

(21) Appl. No.: 12/460,351

(22) Filed: Jul. 18, 2009

(65) Prior Publication Data

US 2010/0016993 A1    Jan. 21, 2010

Related U.S. Application Data

(60) Provisional application No. 61/135,285, filed on Jul. 18, 2008.

(51) Int. Cl.
| | | |
|---|---|---|
| *A61F 2/80* | (2006.01) | |
| *A61F 2/78* | (2006.01) | |
| *A61F 5/01* | (2006.01) | |
| *A61F 2/50* | (2006.01) | |

(52) U.S. Cl.
CPC .............. *A61F 2/7812* (2013.01); *A61F 5/0109* (2013.01); *A61F 2002/5007* (2013.01); *A61F 2002/5053* (2013.01); *A61F 2002/5056* (2013.01); *A61F 2002/7818* (2013.01); *A61F 2250/0014* (2013.01); *A61F 2250/0018* (2013.01); *A61F 2250/0019* (2013.01)

(58) Field of Classification Search
CPC ................... A61F 2/7812; A61F 2002/7818
USPC ............................................... 623/36
See application file for complete search history.

(56) References Cited

U.S. PATENT DOCUMENTS

| | | |
|---|---|---|
| 980,457 A | 1/1911 | Toles |
| 2,325,656 A | 8/1943 | Brophy |
| 2,696,011 A | 12/1954 | Gladik |
| 3,587,572 A | 6/1971 | Evans |
| 3,600,717 A | 8/1971 | McKeehan |

(Continued)

FOREIGN PATENT DOCUMENTS

| | | |
|---|---|---|
| GB | 826 041 | 12/1959 |
| WO | 01/67842 A1 | 9/2001 |

OTHER PUBLICATIONS

Iceross® Confort® Locking/Cushion product information brochure, Mar. 27, 2009, 3 pages.

(Continued)

*Primary Examiner* — Bruce E Snow
*Assistant Examiner* — Melissa Hoban
(74) *Attorney, Agent, or Firm* — Workman Nydegger

(57) ABSTRACT

The liner or sleeve is for use around a joint, for example, as a skin interface between a limb and a prosthetic or orthotic device. The liner or sleeve includes an elastomeric material defining a tubular member to be positioned around a joint. A tendon is attached along a portion of the tubular member to urge the elastomeric material at such portion of the tubular member to contract. The tendon may be integrally molded within the portion of the tubular member. The tendon may be formed of an elastomeric material having a higher durometer hardness relative to the durometer hardness of the tubular member elastomeric material. With the present approach, it is possible to maintain the use of a two part mold while providing a liner or sleeve with enhanced flexion adjacent to a joint area.

20 Claims, 4 Drawing Sheets

(56) References Cited

U.S. PATENT DOCUMENTS

| | | | |
|---|---|---|---|
| 3,601,819 A | 8/1971 | Herrmann | |
| 4,319,413 A | 3/1982 | Mattil | |
| 4,474,573 A | 10/1984 | Detty | |
| 4,635,626 A | 1/1987 | Lerman | |
| 4,885,828 A | 12/1989 | Kozlowski | |
| 4,908,037 A | 3/1990 | Ross | |
| 4,923,474 A | 5/1990 | Klasson et al. | |
| 5,244,716 A | 9/1993 | Thornton et al. | |
| 5,263,923 A * | 11/1993 | Fujimoto | 602/62 |
| 5,308,305 A * | 5/1994 | Romney | 482/124 |
| 5,376,129 A | 12/1994 | Faulkner et al. | |
| 5,503,543 A | 4/1996 | Laghi | |
| 5,507,834 A | 4/1996 | Laghi | |
| 5,603,122 A | 2/1997 | Kania | |
| 5,718,925 A | 2/1998 | Kristinsson et al. | |
| 5,728,167 A * | 3/1998 | Lohmann | 623/36 |
| 5,728,168 A | 3/1998 | Laghi et al. | |
| 5,830,237 A | 11/1998 | Kania | |
| 5,885,509 A | 3/1999 | Kristinsson | |
| 5,885,674 A | 3/1999 | Maemoto et al. | |
| 5,971,729 A | 10/1999 | Kristinsson et al. | |
| 5,972,036 A | 10/1999 | Kristinsson et al. | |
| 6,076,284 A | 6/2000 | Terlizzi | |
| 6,136,039 A | 10/2000 | Kristinsson et al. | |
| 6,171,431 B1 | 1/2001 | Gallagher, Jr. et al. | |
| 6,231,617 B1 * | 5/2001 | Fay | 623/36 |
| 6,406,499 B1 | 6/2002 | Kania | |
| 6,416,703 B1 | 7/2002 | Kristinsson et al. | |
| 6,485,776 B2 | 11/2002 | Janusson et al. | |
| 6,626,952 B2 | 9/2003 | Janusson et al. | |
| 6,706,364 B2 | 3/2004 | Janusson et al. | |
| 6,852,269 B2 | 2/2005 | Eberle et al. | |
| 6,964,688 B1 * | 11/2005 | Kania | 623/36 |
| 6,991,444 B1 | 1/2006 | Laghi | |
| 7,001,563 B2 | 2/2006 | Janusson et al. | |
| 7,025,793 B2 | 4/2006 | Egilsson | |
| 7,105,122 B2 | 9/2006 | Karason | |
| 7,118,602 B2 | 10/2006 | Bjarnason | |
| 7,169,189 B2 | 1/2007 | Bjarnason et al. | |
| 7,291,182 B1 | 11/2007 | Kania | |
| 7,351,264 B2 | 4/2008 | Wilson | |
| 7,438,843 B2 | 10/2008 | Asgeirsson | |
| 2002/0165619 A1 | 11/2002 | Hellberg | |
| 2002/0183859 A1 | 12/2002 | Houser | |
| 2003/0181989 A1 | 9/2003 | Eberle et al. | |
| 2005/0149202 A1 | 7/2005 | Schaffer et al. | |
| 2005/0240283 A1 | 10/2005 | Kania | |
| 2006/0106328 A1 * | 5/2006 | Sieller et al. | 602/21 |
| 2007/0027556 A1 | 2/2007 | Wilson | |
| 2007/0043450 A1 | 2/2007 | Pickering et al. | |
| 2007/0061017 A1 | 3/2007 | Wilson | |
| 2007/0123998 A1 | 5/2007 | Egilsson et al. | |
| 2007/0162153 A1 * | 7/2007 | Barnes et al. | 623/36 |
| 2008/0188949 A1 | 8/2008 | MacKenzie | |
| 2008/0221705 A1 | 9/2008 | Scussel | |
| 2008/0221706 A1 | 9/2008 | Scussel et al. | |
| 2009/0036999 A1 | 2/2009 | Egilsson et al. | |
| 2010/0249949 A1 | 9/2010 | Bjarnason et al. | |
| 2010/0274364 A1 * | 10/2010 | Pacanowsky et al. | 623/36 |
| 2011/0118854 A1 | 5/2011 | Halldorsson | |
| 2012/0150320 A1 | 6/2012 | Bjarnason et al. | |
| 2012/0185060 A1 | 7/2012 | Asgeirsson | |

OTHER PUBLICATIONS

Iceross® Dermo, product information sheets from Internet, http://www.ossur.com/prosthetics/liners/dermo, Mar. 27, 2009, 2 sheets.

Military inStep: Prosthetic Socks and Liners, product information sheets from Internet, http://www.amputee-coalition.org/military-instep/prosthetic-socks, Mar. 27, 2009, 3 pages.

Prosthetic & Orthotic Update NewsLetter, No. 32, Internet Search conducted Mar. 27, 2009, 4 pages.

Walopur® Platilon@U, Product Information Brochure of Epurex Films GmbH & Co., KG, Internet Search result conducted Maarch 27, 2009, 2 pages.

"Material Hardness", 2001, CALCE and the University of Maryland, pp. 1-22; retrieved from http://www.calce.umd.edu/TSFA/Hardness_ad_.htm.

* cited by examiner

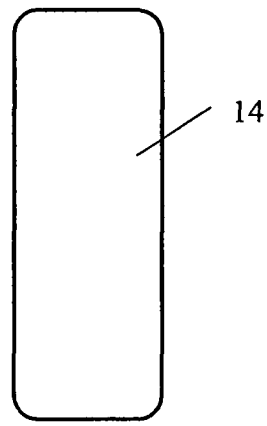
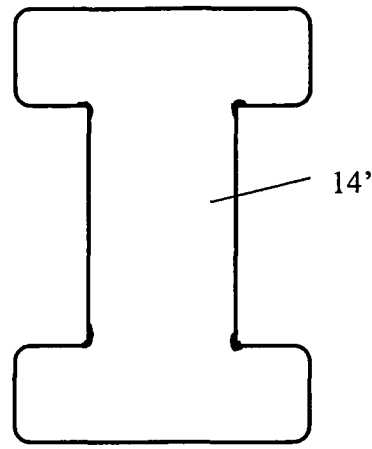
FIG.2A  FIG.2B
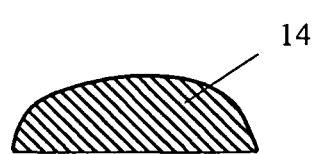
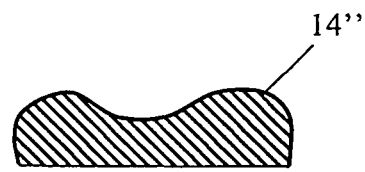
FIG.3A  FIG.3B

FLEXION ENHANCEMENT MEMBER FOR PROSTHETIC OR ORTHOTIC LINER OR SLEEVE AND ASSOCIATED METHODS

CROSS-REFERENCE TO RELATED APPLICATIONS

This application claims the benefit of U.S. provisional application No. 61/135,285 filed Jul. 18, 2008.

BACKGROUND OF THE INVENTION (1) Field of the Invention

The present invention relates to the field of prosthetic and orthotic liners and/or sleeves (i.e. skin-socket interface liners and sleeves), and more particularly to custom and production ("off the shelf") prosthetic liners, sleeves, and associated methods.

(2) Discussion of Related Art

Liners provide a soft, flexible interface between a residual limb of an amputee and a hard socket to which a prosthetic device is secured. Such liners are typically made of an elastomer material such as silicone. Such liners may also be used in connection with orthotic devices. Suspension sleeves are a flexible tube used to secure the prosthetic device to the patients limb. The sleeve may be a sealing sleeve, or a suspension sleeve. Both types start on the prosthetic device and finish on the patients limb. Supportive sleeves can be used in an orthotic device to support a joint or limb of a patient.

Prosthetic suspension liners are described in prior patents, and may be fabricated of elastomer or rubber materials, and are used to cushion a post-operative stump or residual limb with respect to a prosthesis that is installed over the residual limb and coupled to the liner, e.g. by a conventional locking device.

Such liners should conform closely with the residual limb, accommodate all surface contours and sub-surface bone elements of the residual limb, and provide a comfortable cushion between the residual limb and the hard socket of the prosthesis that is to be fitted over the residual limb. Various silicone rubber or elastomer materials are used for suspension liners. Such elastomer materials having an appropriate hardness/softness, elongation, tensile, and other properties, such as bio-inertness (resulting in no skin reaction), have been successfully used for suspension liners.

Similar to liners, orthotic or prosthetic sleeves are provided for supporting and reinforcing muscles, joints, and extremities of patients, and also provide an airtight seal between a residual limb of an amputee and a prosthesis socket worn by the amputee. Moreover, such sleeves are not limited to use for amputees but may be applied to existing limbs to provide support in a manner associated with conventional orthotic devices. These sleeves may be similarly fabricated of elastomer materials. The sleeves may be cylindrical, curved or include other anatomically conforming shapes.

The elastomer forming the liner or sleeve frictionally engages and remains attached to the skin of a residual limb so that the limb is retained within the prosthetic socket in a comfortable, non-irritating manner. For example, liners may be used for any level of amputation both upper and lower limb.

As an example, prosthetic liners are used to cushion the amputee's residual limb from shock during ambulation, however the liner extends higher than the center of the knee to aid in suspension. Such liners are made in most cases with tubular molds or two part molds. To reduce or eliminate any bunching behind the knee during sitting or flexing of the knee, manufacturers have tried several methods of pre-flexing the liner to reduce or eliminate the accumulation of excess material, or bunching, behind the knee. A common conventional method is to produce a bent male and female mold, e.g. as shown in U.S. Pat. No. 5,888,216 to Haberman. The mold includes three or more parts, two or more sections for the female and one or more for the male. This increases the labor and material costs of both the mold and the liner. Three or more part molds are less stable and can increase the rejection rate of the molded liner.

BRIEF SUMMARY OF THE INVENTION

It is an object of the present invention to provide a reliable prosthetic or orthotic skin interface liner or joint sleeve, and associated method of making, with flexion enhancement.

This and other objects, advantages and features in accordance with the present invention are provided by a liner for use as a skin interface between a limb and a prosthetic or orthotic device, the liner comprising: an elastomeric material defining a tubular member to be positioned around a joint; and a tendon attached along a portion of the tubular member to urge the elastomeric material at such portion of the tubular member to contract. The tendon may be integrally molded within the portion of the tubular member.

The tendon may comprise an elastomeric material having a higher durometer hardness relative to the durometer hardness of the tubular member elastomeric material. The elastomeric material may comprise a silicone material or a urethane material, for example. Also, the tubular member may include an open end and a closed end.

Other objects, advantages and features in accordance with the present invention are provided by a sleeve to be worn around a joint, the sleeve comprising: an elastomeric material defining a tubular member to be positioned around the joint; and a tendon integrally formed within a portion of the tubular member to urge the elastomeric material at such portion of the tubular member to contract. The tendon may comprise an elastomeric material having a higher durometer hardness relative to the durometer hardness of the tubular member elastomeric material. The elastomeric material may comprise a silicone or urethane material.

Other objects, advantages and features in accordance with the present invention are provided by a method of making a prosthetic or orthotic device liner or sleeve to be worn around a joint, the method comprising: forming a tendon; forming a tubular member from an elastomeric material, to be positioned around the joint; and attaching the tendon along a portion of the tubular member to urge the elastomeric material at such portion of the tubular member to contract. Attaching the tendon and forming the tubular member may define integrally molding the tendon within the portion of the tubular member.

Integrally molding may comprise stretching the tendon, applying the stretched tendon to a male portion of a mold, and then providing an uncured elastomeric material within a space defined between the male portion and a female portion of the mold, and allowing the uncured elastomeric material to set, cure and bond to the stretched tendon. Forming the tendon may comprise molding the tendon from an elastomeric material having a higher durometer hardness relative to the durometer hardness of the tubular member elastomeric material. Again, the elastomeric material may comprise a silicone material or a urethane material, and the tubular member may be formed with an open end and a closed end.

Thus, with the present approach, it is possible to maintain the use of a two part mold while providing a liner or sleeve with enhanced flexion adjacent to a joint area.

BRIEF DESCRIPTION OF THE SEVERAL VIEWS OF THE DRAWING(S)

FIGS. 2A and 2B are plan views illustrating examples of different shaped tendons.

FIGS. 3A and 3B are cross-sectional views illustrating examples of different tendon cross-sectional shapes.

DETAILED DESCRIPTION OF THE PREFERRED EMBODIMENTS

The following description refers to, by example, a liner associated with the knee, however, the features of the invention apply to liners and sleeves for use with any limb/joint area that may benefit from the use of a flexion enhancement member as described herein. Features of the present invention are directed to a prosthetic or orthotic liner or therapeutic sleeve and associated methods of making and using, and includes the use of an elastomer material, e.g. pourable or injectable silicone, that may be used with a simple mold or press. The silicone is preferably biocompatible, e.g. "healthcare grade" or "medical grade", which is suitable for external use. For example, an appropriate silicone system may also be clear to semi-translucent and curable at room temperature. The molded silicone liner should have high tear strength and exhibit flexibility and high elasticity. Other elastomers with the appropriate features are also contemplated.

Figure 1:
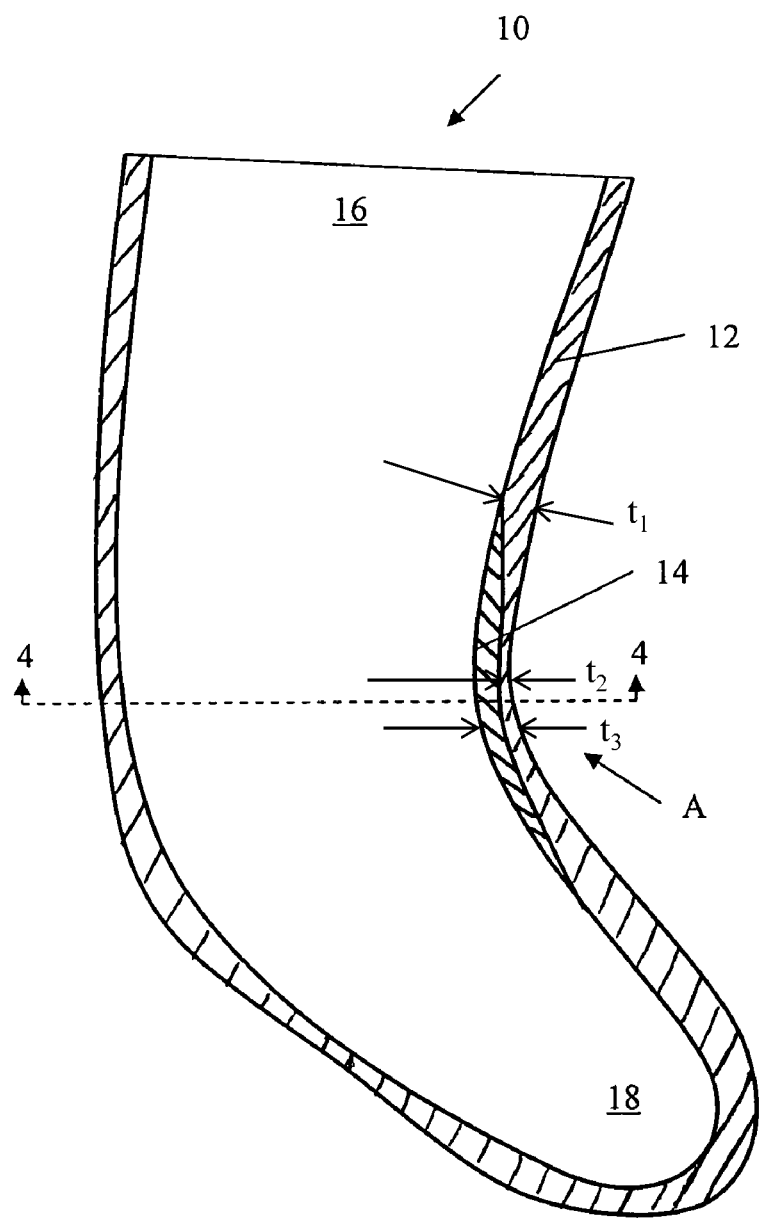
FIG. 1 is a cross-sectional view of a liner including a main body with a tendon and depicting the flexion desired in an areas associated with a joint, e.g. the knee, in accordance with features of the present invention.

Referring to FIGS. 1-6 below, embodiments consistent with features of the present invention will be described. In FIG. 1, a liner 10, e.g. for use as a skin interface between a limb and a prosthetic or orthotic device, is illustrated and includes an elastomeric material defining a tubular member 12 to be positioned around a joint, e.g. a knee joint in a below-knee amputee. A tendon 14 is attached along an area A or portion of the tubular member 12 to urge the elastomeric material at such portion of the tubular member to contract. As will be described in more detail below, the tendon 14 may be integrally molded within the portion A of the tubular member 12.

As shown in FIG. 1, the tubular member 12 defines a first thickness $t_1$ at a first cross-section adjacent the tendon 14 and a second thickness $t_2$ at the cavity portion along a second cross-section of the liner 12. The second thickness $t_2$ is less than the first thickness $t_1$, and the tendon 14 and the tubular member 12 combine to form a third thickness $t_3$ generally the same as the first thickness $t_1$.

Furthermore, the tendon 14 may comprise an elastomeric material having a higher durometer hardness relative to the durometer hardness of the tubular member 12 elastomeric material. The elastomeric material may comprise a silicone material or a urethane material, for example. Also, the tubular member 12 may include an open end 16 and a closed end 18. For example, the Shore A durometer hardness of the tubular member 12 or main body elastomeric material may be in the range of 2-6 and preferably is 4, while the Shore A durometer hardness of the tendon 14 elastomeric material may be in the range of 2-15 and preferably 10.

Figure 4:
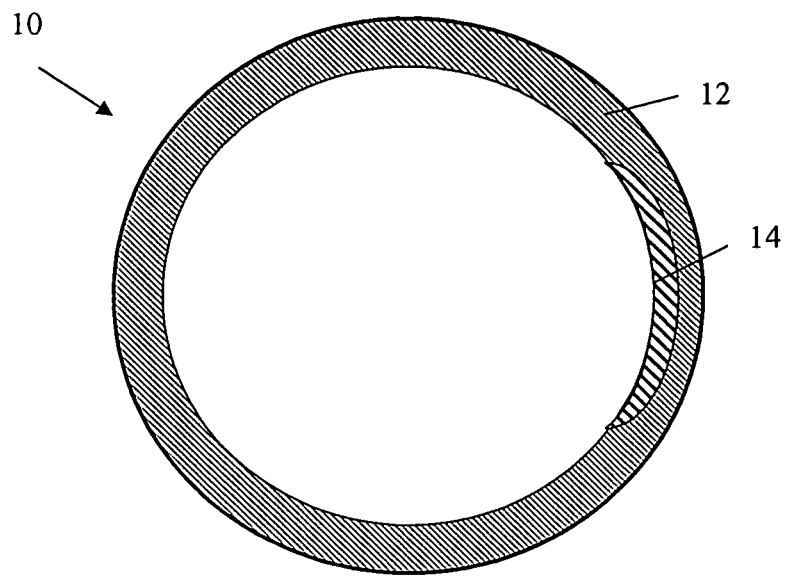
FIG. 4 is a cross-sectional view of the liner in FIG. 1 at the level of the area around the joint taken at line 4-4 of FIG. 1.

The tendon 14 can be formed in any shape suitable to provide the desired flexion but may typically be made rectangular (FIG. 2A) or as a bone shaped tendon 14' (FIG. 2B), for example. Also, various cross-sectional shapes of the tendon that are suitable to provide the desired flexion may include a rounded shaped tendon 14, e.g. as illustrated in FIG. 3A and FIG. 4, or a ribbed shaped tendon 14" (FIG. 3B), for example. The illustrated shapes may be preferable, for example, but other shapes and cross sections are contemplated.

Figure 5:
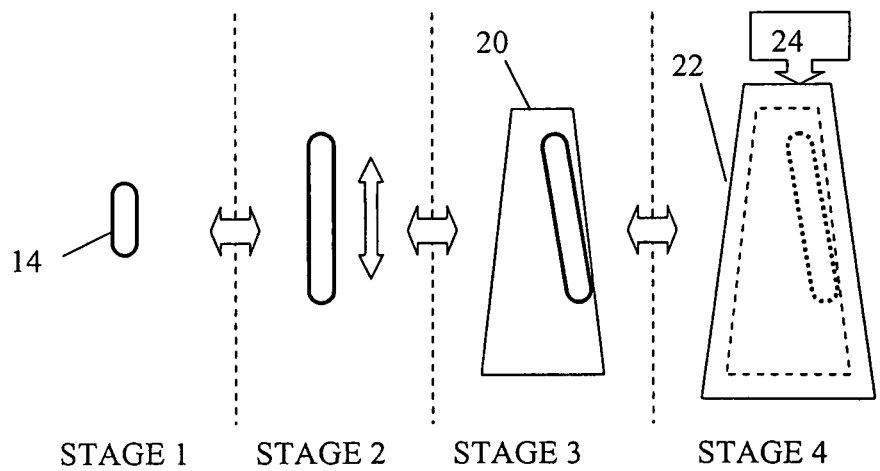
FIG. 5 is a schematic diagram of an embodiment of a manufacturing technique for making the liner of FIG. 1.
Figure 6:
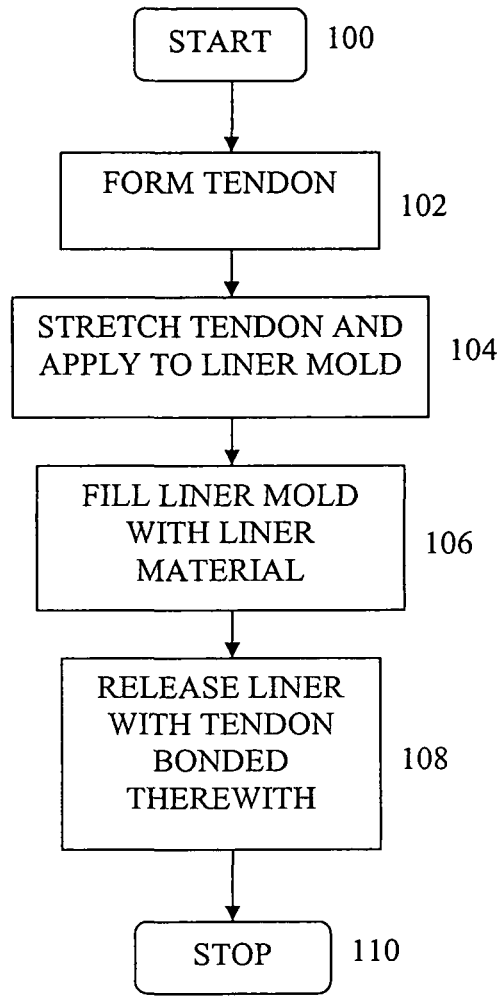
FIG. 6 is a flowchart illustrating the various steps of a method of making the liner of FIG. 1.

Referring more specifically to FIGS. 5 and 6, a method of making the liner 10 will now be described. Illustratively, FIG. 5 includes Stages 1-4, and FIG. 6 includes steps 100-110, of an embodiment of the liner manufacturing process. The method begins (step 100) and at Stage 1 (step 102), a tendon 14 is formed. For example, a suitable mold having a cavity with the desired shape of the tendon 14 is filled with elastomeric material and allowed to set but not fully cure. Then, at Stage 2 (step 104), the tendon, in the green state, is stretched and applied to the liner mold (Stage 3), e.g. the male portion 20 of the liner mold adjacent an area associated with the posterior of a knee joint. The female portion 22 of the liner mold is placed and, at Stage 4, the mold is filled with the elastomeric material 24 to form the tubular member 12 of the liner 14 (Step 106). Unset elastomeric material is filled within a space defined between the male portion 20 and a female portion 22 of the liner mold, and allowed to set, cure and bond to the stretched tendon 14. It may be said that the tendon 14 is integrally molded within the portion A of the tubular member 12.

At Step 108 the liner 12 with the tendon 14 bonded therewith is released, e.g. as illustrated in FIG. 1 before the method ends at Step 110. The area A will then contract due to the tendon 14 being urged to return to its original non-stretched state.

So, in a preferred embodiment, to flex the liner 10 and still maintain the use of a two part mold, a strip or "tendon" 14, e.g. of relatively higher durometer silicone, is applied to the male portion of the mold before being injected with the standard durometer silicone for the main body or tubular member 12 of the liner 10. The liner tendon 14 is stretched before being applied to the mold, and once the injected standard durometer silicone for the main body 12 has set, both the main body 12 and the tendon 14 are bonded. As such, the tendon 14 is integrated within the main body 12. The tendon 14 should be applied to the mold and used before it's full cure time has elapsed, i.e. in the green state, for the two silicones to bond properly, e.g. within 60 minutes of the demold time of the tendon 14. The set, but not fully cured, tendon 14, is still open to bond with the unset liner material. The tendon 14 may be held in place on the mold during formation of the liner with friction and/or the tackiness of the green or non-fully cured silicone, or with a temporary adhesive, for example, or any other suitable securing approach as would be appreciated by those skilled in the art.

Once the liner 10 is removed from the mold, the tendon 14 will be urged to return to it's original shape, and it will pull the other standard durometer silicone of the main body 12 with it causing the liner 10 to contract or shrink in the area A that would be behind the joint, e.g. the knee. As such, the present approach will cause the liner 10 to flex about the area A without the need to use a complicated three or more part mold.

Another advantage to the tendon 14 is the ability to aid the amputee in flexing the joint, e.g. the knee. Conventional liners can impede knee flexion, but with the present invention, during extension the tendon 14 is once again stretched and pulls the liner and amputee's limb back into flexion overcoming the normal resistance of the liner 10.

The tendon 14 may also be made from the same durometer silicone as the main body 12 with a corresponding reduction in the pulling effect or contraction in the area A of the liner 10. Also, it may be possible to form the main body 12 first and then integrate the tendon 14 therewithin and/or to secure the tendon 14 to the female portion of the mold before injecting the elastomer for the main body 12.

Again, the tendon 14 can also be placed into a sealing or suspension sleeve for the same purpose, and the present technique can also be applied to other liner materials such as thermoplastic elastomer and urethane. The tendon 14 of the present approach may also be used in connection with other joint support sleeves and/or braces, for example, sleeves for pre- or post-operative treatment of a joint or for injury prevention or physical therapy. In other words, the tendon 14 would aid the sleeve wearer in the flexing of a joint and also provide resistance during extension of such joint. Such a therapeutic sleeve may also be used to treat arthritis, bursitis, tendonitis and/or meniscal tears, for example.

The present invention was described with references to preferred embodiments of the invention. This invention may, however, be embodied in many different forms and should not be construed as limited to the specific embodiments set forth herein. Rather, these embodiments are provided so that this disclosure will be thorough and complete, and will fully convey the scope of the invention to those skilled in the art. Many modifications and other embodiments of the invention will come to the mind of one skilled in the art having the benefit of the teachings presented in the foregoing descriptions and the associated drawings.

The invention claimed is:

1. A liner for use as a skin interface between a limb and a prosthetic or orthotic device, the liner comprising:
   a tubular member adapted to be positioned around a joint and formed from a first cured mass of elastomeric silicone material, the tubular member forming a cavity portion defined along an inner peripheral surface of the liner and extending into a segment short of a wall thickness of the tubular member such that the wall thickness at the cavity is less than at regions immediately adjacent to the cavity; and
   a tendon having a shape corresponding to the cavity, the tendon attached along and filling the cavity portion such that the will thickness about the cavity surrounds the tendon except for along the inner peripheral surface of the liner, the tendon arranged to urge the tubular member to contract at the cavity portion and form a contracted area, the tendon being formed from a second cured mass of elastomeric silicone material, the tubular member and the tendon forming at least part of the inner peripheral surface of the liner.

2. The liner according to claim 1, wherein the second elastomeric material has a higher durometer hardness than a durometer hardness of the first elastomeric material.

3. The liner according to claim 1, wherein the tubular member includes a proximal open end and a distal closed end, the tendon being confined between the open and closed ends.

4. The liner according to claim 1, wherein the tendon tapers in thickness toward at least one of the proximal and distal ends of the tubular member.

5. The liner according to claim 4, wherein the tendon tapers in thickness toward both the proximal and distal ends of the tubular member.

6. The liner according to claim 1, wherein tubular member defines proximal and distal ends, and a middle area located between the proximal and distal ends, the tendon being confined within the middle area of the tubular member.

7. The liner according to claim 1, wherein the tendon has a variable thickness.

8. The liner according to claim 1, wherein the tubular member defines a first thickness at a first cross-section adjacent the tendon, and a second thickness at the cavity portion along a second cross-section of the liner, the second thickness being less than the first thickness, and the tendon and the tubular member combining to form a third thickness generally the same as the first thickness.

9. The liner according to claim 8, wherein the tendon is located at a posterior knee portion of the liner.

10. The liner according to claim 1, wherein the tubular member and the tendon are integrally molded.

11. The liner according to claim 1, wherein the tendon is located at a posterior knee portion of the liner.

12. A liner for use as a skin interface between a limb and a prosthetic or orthotic device, the liner defining inner and outer surfaces and proximal and distal ends, the liner comprising:
   a tubular member adapted to be positioned around a joint and formed from a first elastomeric material, the first elastomeric material forming a first portion of the inner surface of the liner and defines a cavity extending from the inner surface of the liner a distance into a thickness of the tubular member; and
   a tendon integrally molded and bonded with the tubular member by filling the cavity, the tendon defining a second portion of the inner surface of the liner at only the cavity, the tendon being formed from a second elastomeric material, the second elastomeric material having a higher Shore A hardness than a Shore A hardness of the first elastomeric material and causing the liner to contract to form a contracted area along the outer surface proximate to the tendon between the proximal and distal ends of the liner.

13. The liner according to claim 12, wherein the tubular member includes a proximal open end and a distal closed end, the tendon being confined between the open and closed ends.

14. The liner according to claim 12, wherein the tendon tapers in thickness toward at least one of the proximal and distal ends of the liner.

15. The liner according to claim 12, wherein the tendon tapers in thickness toward both the proximal and distal ends of the liner.

16. The liner according to claim 12, wherein the liner has a middle area located between the proximal and distal ends, the tendon being confined within the middle area of the tubular member.

17. The liner according to claim 12, wherein the tendon has a variable thickness.

18. A liner fir use as a skin interface between a limb and a prosthetic or orthotic device, the liner defining inner and outer surfaces and proximal and distal ends, the liner comprising:
   a tubular member adapted to be positioned around a joint and formed from a cured first elastomeric material, the first elastomeric material forming a localized cavity along an inner periphery of the liner; and
   a tendon directly bonded to the tubular member and filling the cavity of the tubular member such that a portion of the tendon forms part of the inner the inner periphery of the liner at the cavity, the tendon being formed from a cured second elastomeric material having a higher durometer hardness than a durometer hardness of the first elastomeric material;

wherein the hardness differences among first and second elastomeric materials cause the tubular member to form a contracted area proximate to the tendon such that the liner has multiple axes;

wherein the first and second elastomeric materials are selected from the group consisting of silicone and urethane;

wherein the tendon is configured in shape to correspond to a shape of the cavity, both the tendon and tubular member taper in thickness conversely at the cavity.

19. The liner according to claim 18, wherein the tubular member and the tendon are integrally molded.

20. The liner according to claim 18, wherein the tendon is only located at a posterior knee portion of the liner.

* * * * *